United States Patent [19]
Taylor et al.

[11] Patent Number: 6,073,498
[45] Date of Patent: *Jun. 13, 2000

[54] FLUID SAMPLING SYSTEM

[75] Inventors: Stephen John Taylor, Amersham; Robert Fagan Donat Bradshaw, Hemel Hempstead, both of United Kingdom

[73] Assignee: Graseby Dynamics Limited, United Kingdom

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/178,238

[22] PCT Filed: Jul. 10, 1992

[86] PCT No.: PCT/GB92/01259

§ 371 Date: Nov. 14, 1994

§ 102(e) Date: Nov. 14, 1994

[87] PCT Pub. No.: WO93/01485

PCT Pub. Date: Jan. 21, 1993

[30] Foreign Application Priority Data

Jul. 12, 1991 [GB] United Kingdom .................... 9115053

[51] Int. Cl.⁷ ...................................................... G01N 1/24

[52] U.S. Cl. ..................................... 73/864.35; 73/864.34; 73/863.83; 73/864.51

[58] Field of Search ............................. 73/864.52, 864.51, 73/864.33, 863.86, 863.83, 864.34, 864.35, 864.15, 864.11, 864.12, 864.22, 864, 863.24

[56] References Cited

U.S. PATENT DOCUMENTS

| | | | |
|---|---|---|---|
| 3,093,001 | 6/1963 | Williams | 73/864.34 |
| 3,501,964 | 3/1970 | Drummond et al. | 73/864.15 |
| 4,527,953 | 7/1985 | Baker et al. | 73/864.34 |
| 4,531,895 | 7/1985 | Zeck | 417/401 |
| 4,745,801 | 5/1988 | Luzier | 738/863.24 |
| 4,834,110 | 5/1989 | Richard | 128/760 |
| 5,038,623 | 8/1991 | Zeh | 73/863.83 |
| 5,297,432 | 3/1994 | Traina et al. | 73/864.34 |
| 5,312,757 | 5/1994 | Matsuyama et al. | 73/864.11 |
| 5,475,217 | 12/1995 | Bradshaw | 250/287 |
| 5,811,059 | 9/1998 | Genovese et al. | 73/23.42 |

FOREIGN PATENT DOCUMENTS

| | | | |
|---|---|---|---|
| 84102658 | 3/1984 | European Pat. Off. | |
| 87116861 | 11/1987 | European Pat. Off. | G01N 1/10 |
| 8509598 | of 0000 | France | |
| 453606 | 12/1974 | U.S.S.R. | 73/864.34 |
| 2 052 750 | 6/1979 | United Kingdom | G01N 1/22 |
| 2214449 | 9/1989 | United Kingdom | 73/864.34 |

OTHER PUBLICATIONS

Graseby Ionics Pamphlet titled "CAM Chemical Agent Monitor" publication date unknown.

Reactant Ions in Negative Ion Plasma Chromatography by Glenn E. Spangler and Charles I. Collins published at pp. 393 to 402 of Analytical Chemistry, vol. 47, No. 3, Mar. 1975.

Developments in Ion Mobility Spectrometry by G.E. Spangler, D.N. Campbell, K.N. Vora and J.P. Carrico, published by pp. 17 to 28 of ISA Transactions, vol. 23, No. 1, Copyright 1984.

*Primary Examiner*—Hezron Williams
*Assistant Examiner*—Nashmiya S. Fayyaz
*Attorney, Agent, or Firm*—Chan Law Group LC; Steve A. Wong

[57] ABSTRACT

A fluid sampling system has a fluid enclosing element, such as drift cell (60), enclosing a volume of a first fluid. A body of a second fluid, for example in an inlet chamber (62), communicates with the body of first fluid via a small orifice (74). A series of negative pressure pulses is applied to the first fluid by an electromechanical transducer (92), each negative pulse causing a sample of the second fluid to be drawn in through the orifice (74). The sample is then entrained into the air flow of a closed loop circulatory system, and can be detected or measured by any appropriate equipment such as an ion mobility spectrometer.

5 Claims, 5 Drawing Sheets

6,073,498

FLUID SAMPLING SYSTEM

TECHNICAL FIELD

The present invention relates to a fluid sampling system for effecting the transfer of samples of a second fluid from a body of that fluid into a system incorporating an enclosed volume of a first fluid. The first fluid may or may not circulate within the system.

DISCLOSURE OF THE INVENTION

Such fluid sampling systems are commonly employed in analytical instruments e.g. chromatographs and mass spectrometers where it is needed to transfer for analysis a small sample of gas, vapour or liquid of interest.

Such fluid sampling systems may also be employed, for example, in atmospheric monitoring or analysis equipment where a sample or samples of an ambient atmosphere are to be transferred into a closed loop circulatory system within the equipment and examined for the presence of components of interest.

Atmospheric monitoring equipment of this general type is described in UK Patent No. 2052750 in which an external atmosphere is sampled by drawing a flow of the external atmosphere over a membrane through which a sample of the atmosphere permeates into a closed loop circulatory system and is entrained in the closed loop gas flow, and conveyed to means for detecting and/or identifying vapours or gases of interest in the entrained sample.

Membrane inlet systems, such as employed in the equipment described in UK Patent No. 2052750, suffer a number of significant disadvantages. For example the membrane employed in such systems has a slow response to sampling commands, tends to retain sample from one sampling to the next, and often requires local heating to optimise sample permeation through it. Most inconveniently the transmission characteristics of the membrane cannot be varied, for example to permit variation of instrumental sensitivity or dynamic measurement range.

It is an object of the present invention to provide a novel fluid sampling system in which the disadvantages of such prior art sampling systems are largely overcome or at least mitigated.

According to an aspect of the present invention there is provided a fluid sampling system comprising fluid enclosing means arranged to enclose a volume of a first fluid into which a sample of a second fluid is to be introduced, the fluid enclosing means having an orifice via which the second fluid may be drawn into the fluid enclosing means, and pressure pulse means arranged to apply a negative pressure pulse to the first fluid whereby a sample of the second fluid is drawn into the fluid enclosing means through the orifice. To put it in other words, the invention provides a sample inlet system of the type referred to in which the body of the fluid to be sampled is separated from the enclosed fluid volume into which a sample of the body of fluid is to be transferred, by means including an orifice, and in which means are provided for applying a pressure pulse to the enclosed fluid volume whereby a sample of the fluid body is drawn into the enclosed fluid volume through the orifice. Continuous transfer may be effected by applying a repetitive pressure pulsing to the system incorporating the enclosed fluid volume.

Although repetitive pulsing will cause fluid flow through the orifice from the body of the fluid into the enclosed fluid volume and vice versa, sample material incoming to the enclosed fluid volume will be impelled into the enclosed fluid volume or, in the case of there being a circulatory flow within the system incorporating the enclosed fluid volume, will be entrained in the flow and conveyed away from the orifice, resulting in each case in a net flow of sample fluid into the enclosed fluid volume.

The rate at which sample material is transferred through the orifice may be controlled by variation of the amplitude, the repetition rate, or the duration of, the pressure pulses, or by a combination of two or more of those parameters.

The rate of transfer of sample material through the orifice may be controlled automatically by controlling one or more of the parameters of the pressure pulses applied to the system incorporating the enclosed fluid volume in response to a measured value of the transferred fluid sample or of a component of interest in the transferred fluid sample.

The pressure pulses applied to the system incorporating the enclosed fluid volume may be generated by means of an electromechanical transducer in which an applied electrical signal generates a mechanical displacement capable of producing pressure pulsing of the system. By varying the characteristics of the electrical drive signal to the transducer, the parameters of the pressure pulses may be similarly varied.

The electromechanical transducer may be such as to produce pressure variations in the system by positional variation of a diaphragm in response to the electrical signal applied to means displacing the diaphragm.

Such a transducer may be mounted in the system incorporating the enclosed fluid volume with the diaphragm in direct contact with the fluid in the system thereby enabling pressure pulses to be applied directly to the fluid.

BRIEF DESCRIPTION OF THE DRAWINGS

The invention may be carried into position in a number of ways and two specific embodiments will now be divided, by way of example, with reference to the drawings, in which.

DETAILED DESCRIPTION OF THE INVENTION

Figure 1:
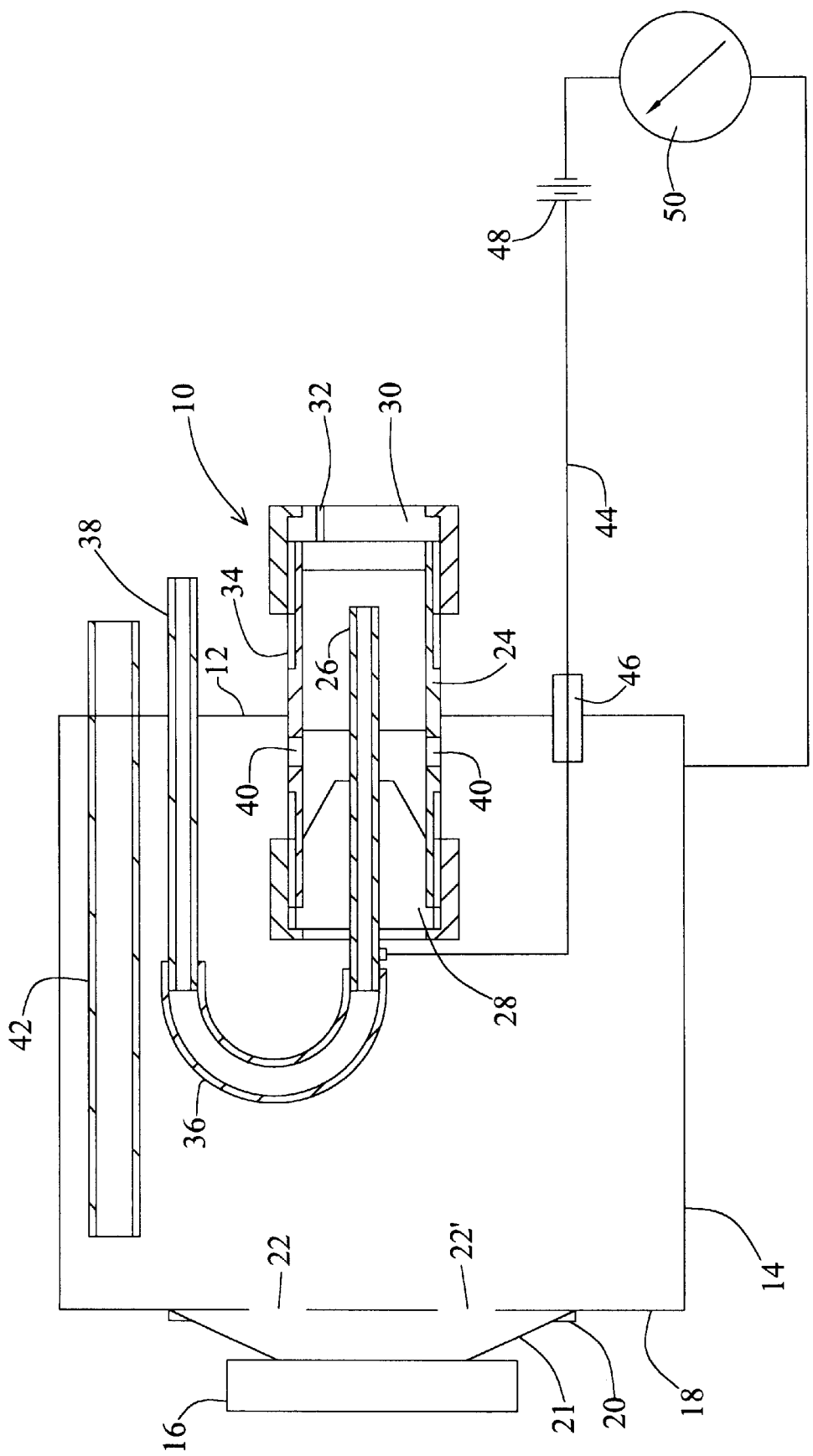
FIG. 1 is a diagrammatic representation of a fluid sampling system in accordance with a first embodiment of the invention in association with an electron capture detector.

Referring to FIG. 1, an electron capture detector indicated generally at 10 is mounted through one end wall 12 of an enclosure 14, and a small loudspeaker 16 forms part of the exterior of the other end wall 18.

The rim 20 of the loudspeaker 16 is sealed to the exterior of the end wall 18 and the volume enclosed by the loudspeaker cone 21 communicates with the interior of the enclosure 14 through apertures 22,22' in the end wall 18.

The electron capture detector 10 comprises a tubular electrically-conducting outer body 24, and an inner electrode 26 mounted in the outer body 24 by means of an electrically insulating mount 28. The opposite end of the body 24 is closed by a plug 30 in which there is a pin-hole aperture 32 which communicates with the interior of the body 24. The ionizing source for the detector is a cylindrical ten-millicurie Nickel-63 foil sleeve 34 surrounding the open end of the inner electrode 26 which is tubular and connected via a flexible electrically insulating coupling 36 to an inlet pipe 38 through which carrier gas for the detector 10 is introduced. Carrier gas from the detector exits the body 24 through apertures 40 and leaves the enclosure 14 through a pipe 42 also mounted in the end wall 12.

Electrical connection is made to the inner electrode 26 by way of a lead 44 which passes through the end wall 12 in the insulating sleeve 46.

The electrical circuit of the detector is completed by a DC source 48 and current indicating means shown diagrammatically at 50.

The function and operation of the electron capture detector is well known. Briefly, in the absence of a sample in the body of detector 10 a standing current is established in the external electrical circuit due to ionization of a non-electron-capturing carrier gas such as nitrogen introduced through the electrode 26, by the ionising source 34. In the presence of an electron-capturing sample material introduced into the detector, the standing current reduces by an amount related to the nature and quantity of the sample introduced.

Sample flow into the detector 10 is effected through the aperture 32 and is achieved by application of a varying pressure to the internal volume of the enclosure 14 by the electrical energisation of the loudspeaker 16 causing the cone 21 to move in accordance with the energisation and thereby apply a pressure pulse to the inner volume of the enclosure 14 which is communicated to the inner face of the plug 30 via the apertures 40 in the detector body 24.

Application of a suitably polarised drive potential to the motor of the loudspeaker 16 to cause the cone 21 to move outwardly from the end face 18 results in a negative pressure pulse being communicated to the interior of the enclosure 14 and hence to the inner end of the pin-hole aperture 32, causing a sample of the atmosphere adjacent the exterior of the plug 30 to be drawn into the detector 10 and moved through the ionising region of the detector under the influence of the carrier gas which is flowing from the mouth of the electrode 26 toward the apertures 40. Removal or reversal of the drive potential on the motor of the loudspeaker will cause the cone 21 to move towards the end face 18 and result in the expulsion from the interior of the enclosure 14 through the pin-hole aperture 32 of a similar volume of the enclosed atmosphere to that of the external atmosphere previously drawn in.

If a stream of sample gas from the exterior of the enclosure 14 is required to be introduced into the detector 10 this is achieved by application of a repetitive drive signal to the motor of the loudspeaker 16 causing repetitive movement of the cone 21 and thus repetitive pulsing of the inner atmosphere of the enclosure 14. This will result in the repetitive drawing in of samples of the atmosphere from the exterior of the enclosure 14 which, by the appropriate choice of parameters for the whole system, will enable a net transfer of sample gas from the exterior into the detector 10 as incoming samples will be swept from the region of the plug 30 by the carrier gas flow following each inspiration and the atmosphere expelled through the pin-hole aperture 32 will be largely composed of carrier gas from the electrode 26.

The tube 42 is chosen with dimensions to offer a minimal resistance to the outflow of carrier gas and sample mixture from the enclosure 14 but, due to the mass of gas contained within it, maximum impedance to pressure pulses developed by the loudspeaker 16.

In the system described in relation to FIG. 1, the aperture 32 was 2 mm long and 0.79 mm in diameter. The external dimensions of the enclosure 14 were 80 mm long by 60 mm in diameter. The tube 42 was 50 mm long and 3 mm in diameter.

Nitrogen carrier gas was introduced into the detector through the electrode 26 at a flow-rate of 1.67 mls per second.

The loudspeaker 16 with a nominal cone diameter of 50 mm was driven with a sine-wave signal of 60 Hz from a variable frequency oscillator, and the amplitude of the drive signal varied to vary the rate of introduction of air through the pin-hole aperture 32.

Figure 2:
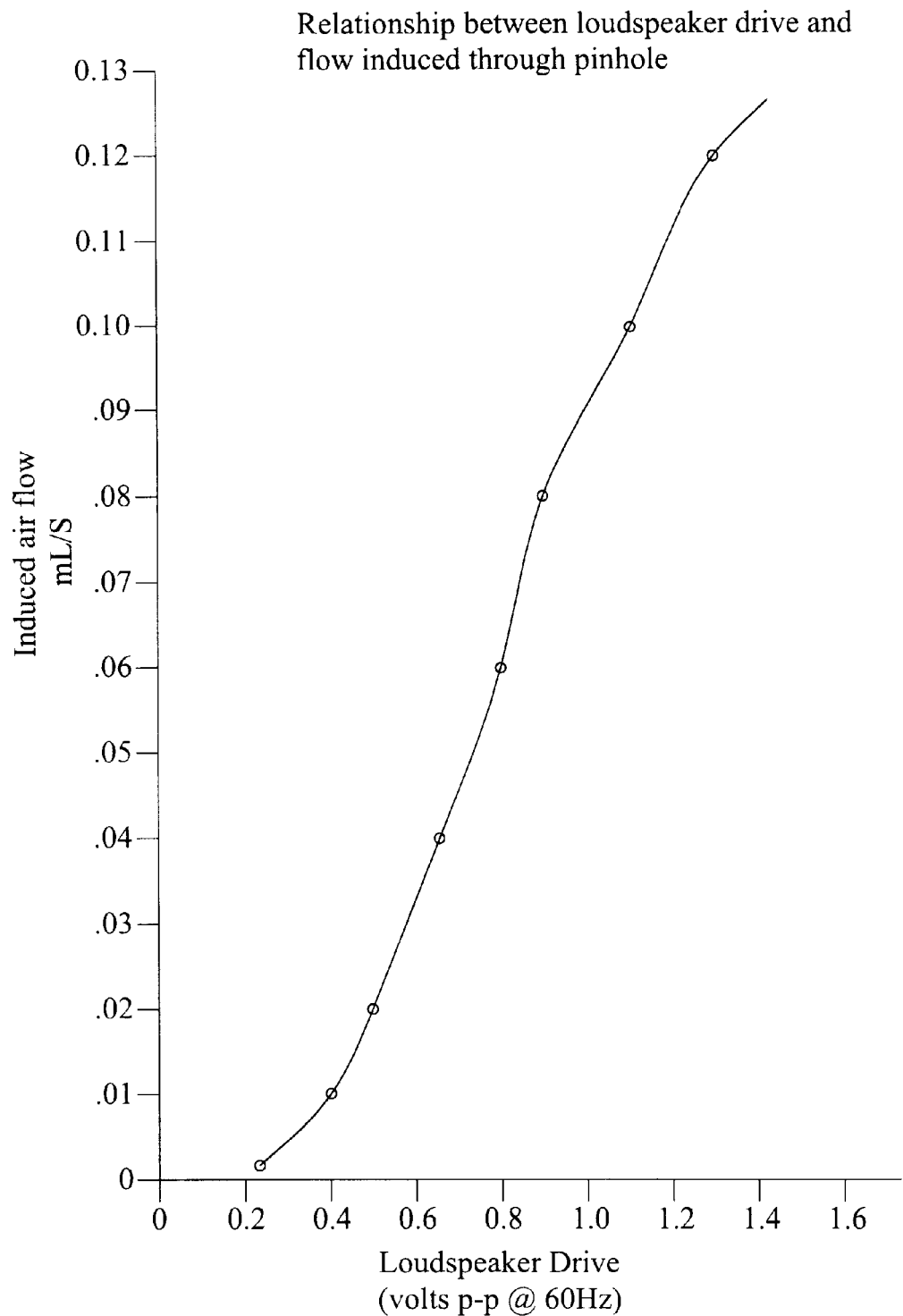
FIG. 2 is a plot of inlet flow through the sampling system of FIG. 1.

The relationship between the electron capture detector current and air flow through the aperture 32 was determined by a separate experiment in which a measured flow of air was applied to the aperture 32 and the resulting current noted. The air flow caused by the loudspeaker 16 was then deduced from the change in electron capture detector current. Hence the plot shown in FIG. 2 was derived in which the induced air flow versus the peak-to-peak value of the drive signal at a constant 60 Hz is plotted. From this figure it will be seen that within the chosen drive signal range, a near-linear relationship between drive signal and induced airflow is demonstrated.

Figure 3:
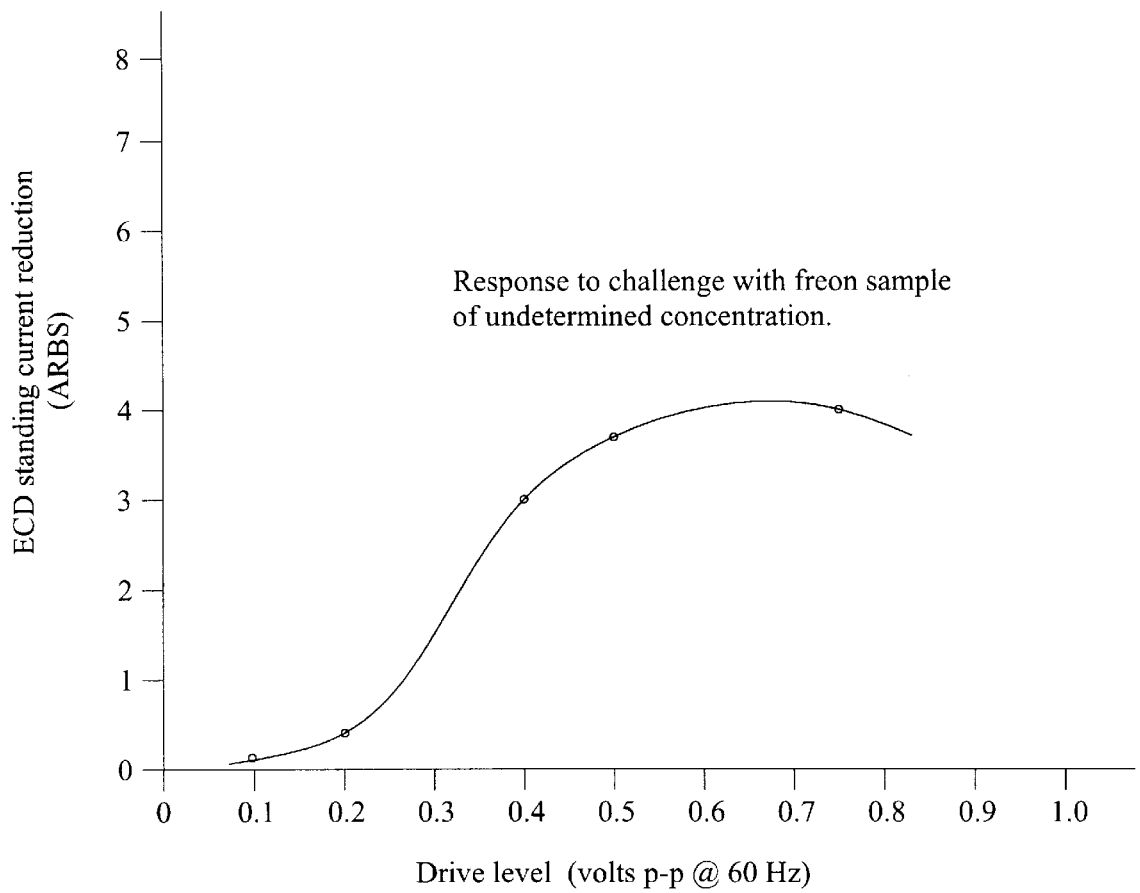
FIG. 3 is a plot of detector current with an electron-capturing sample material in the region adjacent the exterior of the sample inlet.

When freon gas of undetermined concentration was introduced into the region of the exterior of the aperture 32 the reduction of detector standing current against the peak-to-peak drive signal at a constant 60 Hz was as shown in the plot of FIG. 3.

Employment of a fluid sampling system in accordance with an embodiment of the invention, in an ion mobility spectrometer, offers a number of advantages over arrangements currently used which most commonly employ a membrane inlet system such as is described and illustrated in UK Patent No. 2052750.

Figure 4:
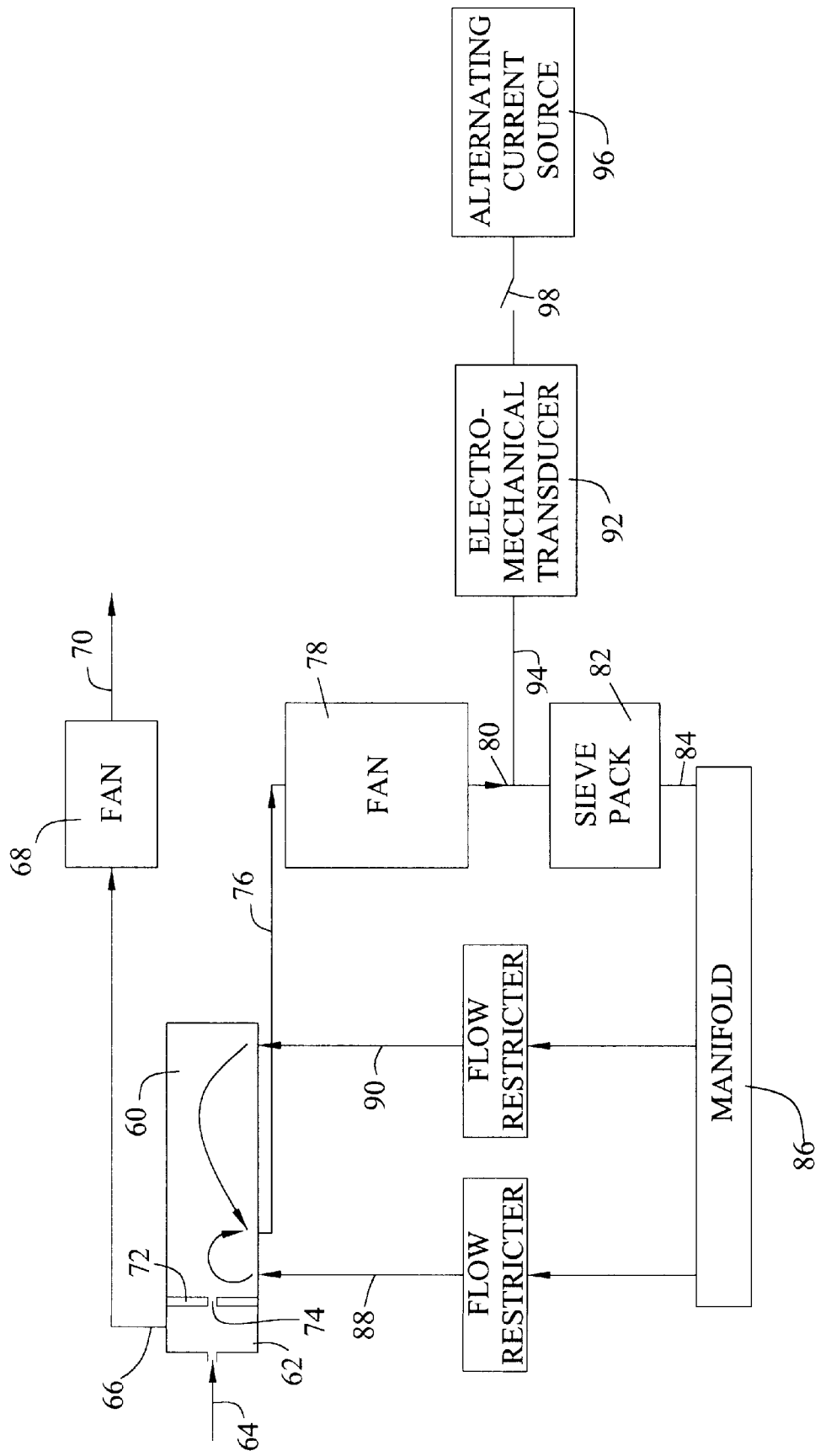
FIG. 4 is a schematic representation of an ion mobility spectrometer using a fluid sampling system in accordance with a second embodiment of the invention.

A schematic diagram of an ion mobility spectrometer employing a fluid sampling system in accordance with the invention is shown in FIG. 4. The function and use of such instruments is well known in the art, for example from UK Patent Application No. 2217103A, and will not be further described here except to the extent necessary to illustrate the application of the present invention hereto.

Referring to FIG. 4, an ion mobility drift cell 60 has an inlet chamber 62 adapted to receive a flow of gas or vapour 64 which is drawn through the chamber 62 to an outlet 66 by means of a fan or pump 68 and exhausted at a vent 70. Preferably a fan 68 is used rather than a pump to avoid undesirable pressure oscillations arising with the system.

The drift cell 60 is separated from the inlet chamber 62 by a wall 72 in which there is a pin-hole aperture 74.

The drift cell 60 is connected into a closed loop circulatory carrier gas system comprising return flow line 76, a recirculatory fan or pump 78, a transfer line 80, a sieve pack 82, a transfer line 84, a manifold 86, a source flow line 88 and a drift flow line 90. Preferably a fan 78 is used rather than a pump, to avoid undesirable pressure oscillations arising within the system. The circulatory carrier gas is air.

An electromechanical transducer 92 is pneumatically coupled to the line 80 and between the fan 78 and the sieve pack 82 through a line 94 and is driven from a source of alternating current 96 connected to it by a switch 98 to produce repetitive pressure pulsing of the line 80 and thus of the whole closed loop circulatory system when switch the 98 is closed. The transducer could be located elsewhere within the sealed circulatory system.

In operation, with the switch 98 open, a flow of external atmosphere 64 is drawn through the inlet chamber 62 into the line 66, through the fan 68 and is returned to atmosphere through the vent 70. Only a little of the inlet flow enters the drift cell 60 through the pin-hole aperture 74, as the dimensions of the aperture 74 constitute a large diffusion barrier to entry. Alternatively (not shown), gas could be injected into the chamber 62 from a high-pressure source and vented to atmosphere without the use of the fan 68.

The aperture 74 is 0.9 mm in depth and 0.3 mm in diameter. The exact dimensions are not critical but of course the smaller and deeper the hole the greater the resistance against diffusion from the inlet chamber 62, and the smaller the sample drawn in at each pressure pulse. The aperture should not be so large that bulk flow of gas is possible through it, except when a pressure pulse is applied. Larger apertures of course need smaller pressure pulses for a given sample size.

A circulatory flow of carrier gas, for example dry air, is maintained in the sealed circulatory loop by the fan 78. A primary flow passes into the drift cell 60 from the source flow line 88 into the region of the wall 72 passing through the reaction chamber part of the cell and exhausting to the return flow line 76. A secondary flow passes into the collector region of the drift cell 60 and passes down the length of the drift cell 60 also to exhaust to the return flow line 76.

With the switch 98 closed repetitive pressure pulses (e.g. at a few tens of hertz) are applied to the circulatory loop, and via the loop to the region in the drift cell 60 adjacent the wall 72 and the pin-hole aperture 74. Successive negative-going pulses will cause successive samples of the inlet flow 64 to be drawn from the chamber 62 through the aperture 74 into drift cell where they are entrained in the source flow and swept through the reaction chamber of the cell 60 to the return flow line 76. Positive-going pressure pulses will eject a discrete amount of carrier gas from the cell 60 through the aperture 74 but little or none of the previously incoming sample of inlet flow, resulting in a net inflow of samples from the external atmosphere into the cell 60 for detection and or measurement.

It will be appreciated that the magnitude of the sample flow entering into the drift tube 60 will be controllable by control of the drive signal applied to the transducer 92 from the supply 96.

It will also be appreciated that the drive signal applied to the transducer 92 could by means of a suitable feedback loop be varied in dependence upon the magnitude of the electrical output signal derived from the drift tube 60 such as to increase or decrease the amount of sample incoming to the tube 60, thereby controlling the sensitivity or dynamic range of the instrument in a manner well known per se in the art. Also, if the drive signal is removed, the behaviour of the IMS cell 60 in the absence of sample flow through the aperture 74 can be monitored.

Figure 5:
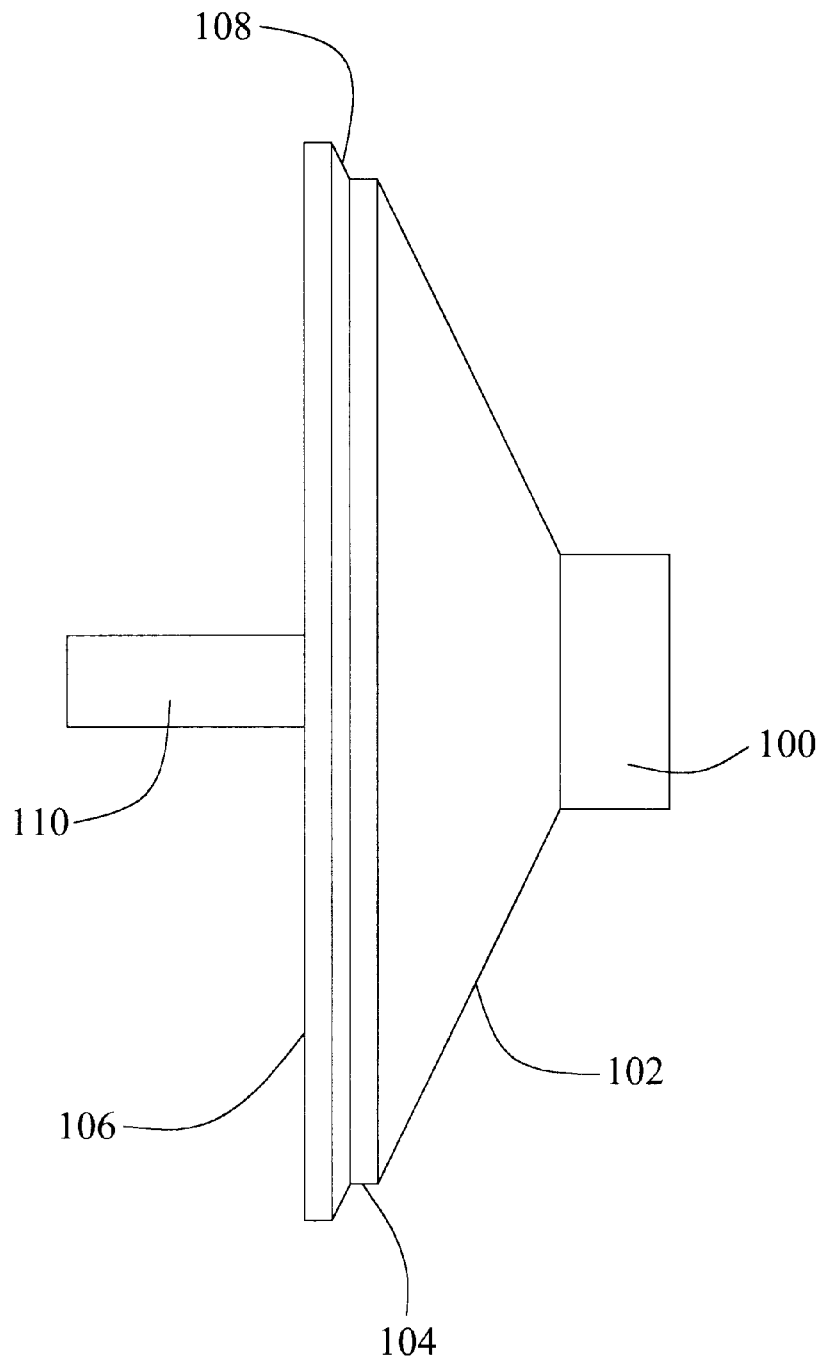
FIG. 5 is a diagrammatic representation of the electro-mechanical transducer system employed in the spectrometer of FIG. 4.

FIG. 5 shows schematically a suitable electromechanical transducer for use in the ion mobility spectrometer described with reference to FIG. 4. The transducer is a modified loudspeaker comprising a motor 100, and a frame 102 supporting a moving cone (not shown) attached to a rim 104. The airspace forward of the cone is sealed by means of a plate 106 glued to the rim 104 by glue 108 to give a hermetically sealed enclosure, the only communication to which is through a pipe 110 mounted into a suitable aperture in the plate 106. The pipe 110 is coupled to the line 94 of FIG. 4 which in turn is connected to the closed loop circulatory system of the ion mobility spectrometer.

Although the invention has been described with specific reference to provision of pressure pulsing by use of an electromechanical acoustic transducer, it will be apparent that other means of providing the requisite pressure pulsing may be employed, for example, a piezo-electric actuator where an applied electrical signal produces a mechanical deformation of the crystal which could be applied to a flexible conduit to produce the necessary pressure pulsing.

Embodiments of the invention could be used as continuously or repeatingly operated detectors in a process line, or could be used for continuous or user-controlled detection of small quantities of noxious or other gases in the ambient atmosphere.

The invention may also be used other than in the context of analytical instrumentation, for example for introducing a controlled quantity of a gas or vapour of known concentration into an enclosed static or flowing body of gas or vapour, or to permit injection of a controlled amount of a gas, vapour or liquid into another medium, for example in a chemical process plant. Embodiments of the invention could be used to provide liquid samples into a static or flowing body of liquid. They could also provide liquid samples into a static or flowing body of air or other gas.

We claim:

1. A fluid sampling system for extracting a fluid sample from a body of fluid, the system comprising fluid enclosing means arranged to enclose a volume of a first fluid into which a sample of a second fluid is to be introduced, the fluid enclosing means comprising a substantially closed chamber having an orifice via which the second fluid may be drawn into the fluid enclosing means, and means for drawing the sample of the second fluid into the volume of first fluid through the orifice, comprising a loudspeaker including a diaphragm arranged to apply a negative pressure pulse to the first fluid, and in which the negative pressure pulse applied to the first fluid is applied directly to the second fluid via the orifice, whereby a differential pressure is caused to exist across the orifice.

2. A fluid sampling, system as recited in claim 1, including means for selectively adjusting the loudspeaker to vary the amplitude of the pressure pulse.

3. A fluid sampling system as recited in claim 1, including means for selectively adjusting the loudspeaker to vary the duration of the pressure pulse.

4. A fluid sampling system as recited in claim 1, including driving means arranged to drive the loudspeaker repetitively, so effecting repeated transfers of samples of the second fluid into the fluid enclosing means.

5. A fluid sampling system as recited in claim 1, including means for adjusting the driving means so as selectively to vary a repetition rate of the loudspeaker.

* * * * *